(12) United States Patent
Akiyama

(10) Patent No.: US 7,507,765 B2
(45) Date of Patent: Mar. 24, 2009

(54) GERANYL COMPOUNDS

(75) Inventor: Kiyoshi Akiyama, Komatsu (JP)

(73) Assignee: Ohgen Research Laboratories, Ltd., Ishikawa (JP)

( * ) Notice: Subject to any disclaimer, the term of this patent is extended or adjusted under 35 U.S.C. 154(b) by 156 days.

(21) Appl. No.: 11/356,019

(22) Filed: Feb. 17, 2006

(65) Prior Publication Data
US 2006/0142244 A1  Jun. 29, 2006

Related U.S. Application Data

(62) Division of application No. 10/498,882, filed as application No. PCT/JP02/13615 on Dec. 26, 2002, now Pat. No. 7,125,852.

(30) Foreign Application Priority Data

| Jan. 11, 2002 | (JP) | ................. 2002-4123 |
| Jan. 11, 2002 | (JP) | ................. 2002-4131 |
| Jan. 11, 2002 | (JP) | ................. 2002-4136 |
| Sep. 27, 2002 | (JP) | ............. 2002-283644 |

(51) Int. Cl.
 *A01N 37/12* (2006.01)
 *A01N 37/44* (2006.01)
 *A61K 31/195* (2006.01)
(52) U.S. Cl. .................... 514/563; 514/561
(58) Field of Classification Search ............... None
See application file for complete search history.

(56) References Cited

U.S. PATENT DOCUMENTS

2004/0053288 A1 * 3/2004 Yanai et al. ............ 435/6

FOREIGN PATENT DOCUMENTS

| EP | 0091694 | 10/1983 |
| EP | 0534546 | 3/1993 |
| EP | 0670317 | 9/1995 |
| JP | 09-40687 | 2/1997 |
| WO | 95/33847 | 12/1995 |

* cited by examiner

*Primary Examiner*—Traviss C McIntosh, III
(74) *Attorney, Agent, or Firm*—Wenderoth, Lind & Ponack, L.L.P.

(57) ABSTRACT

This invention provides compounds having excellent antitumor activity, which are represented by the following formulae in which $R^1$, $R^2$, $R^3$, m, n and $R^4$ have the significations as given in the specification.

5 Claims, No Drawings

GERANYL COMPOUNDS

This application is a divisional of U.S. application Ser. No. 10/498,882, filed Jun. 16, 2004, now U.S. Pat. No. 7,125,852 which is a national stage application of International Application No. PCT/JP02/13615, filed Dec. 26, 2002.

TECHNICAL FIELD

This invention relates to novel geranyl compounds or mevalonic acid derivatives, and to their utilization as antitumor agents.

BACKGROUND ART

Many geranyl compounds having 1,5-diene structure are present in vivo, and are known as in vivo precursors of substances having polyene structure and exhibiting various physiological activities. These substances having 1,5-diene structure and polyenes derived therefrom invariably start from mevalonic acid and biosynthesized.

I noticed, as such geranyl compounds having 1,5-diene structure, geranic acid or geranylamine, and furthermore mevalonic acid which is the base for biosynthesis of polyenes, synthesized various derivatives of geranic acid or geranylamine and mevalonic acid and investigated their physiological activities, in particular, antitumor activity and toxicity, and have come to complete the present invention.

DISCLOSURE OF THE INVENTION

This invention provides geranyl compounds represented by the following formulae (I-1), (I-2) or (I-3):

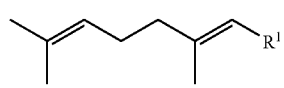

(I-1)

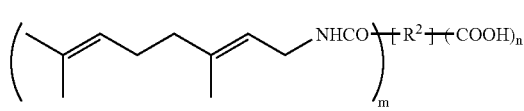

(I-2)

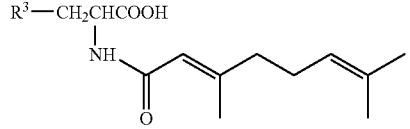

(I-3)

in which $R^1$ stands for

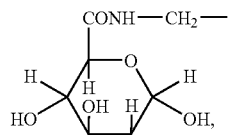 , 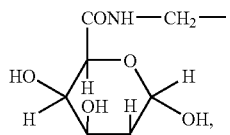

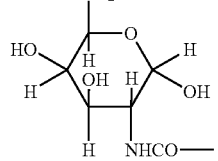 , 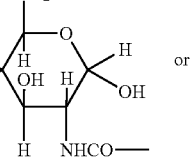 or

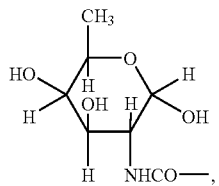

$R^2$ stands for a residual group remaining after removing all carboxyl groups present in a carboxylic acid selected from the group consisting of malic acid, citric acid, succinic acid, fumaric acid, 2-oxoglutaric acid, pyruvic acid, p-pyruvoaminobenzoic acid, retinoic acid, tyrosine, cysteine, glutamic acid and serine, and where hydroxyl or amino group(s) are present in the residual group, they may optionally be protected by acyl (e.g., lower alkanoyl) or benzyloxycarbonyl group(s), m is 1, 2 or 3, n is 0, 1 or 2, m+n showing the number of carboxyl groups which are present in said carboxylic acid, and $R^3$ stands for p-hydroxyphenyl or mercapto group.

The invention also provides mevalonic acid derivatives represented by the following formula (I-4):

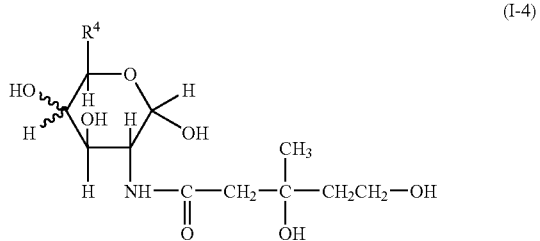

(I-4)

in which $R^4$ stands for —$CH_2OH$ or —$CH_3$.

Those geranyl-sugar derivatives of above formula (I-1) include the following five compounds:

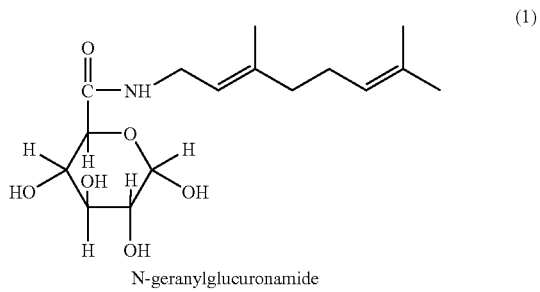

(1)

N-geranylglucuronamide

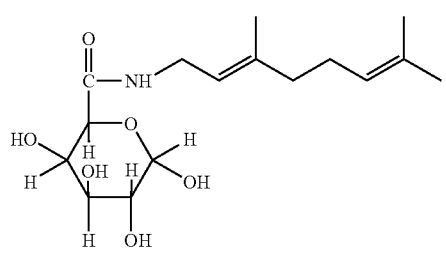

(2) N-geranylgalacturonamide

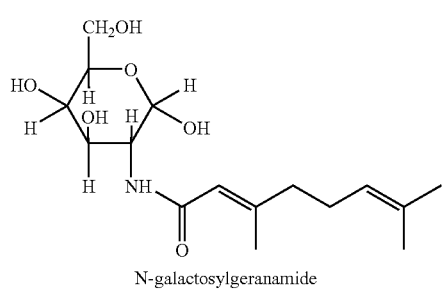

(3) N-galactosylgeranamide

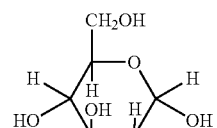

(4) N-glucosylgeranamide and

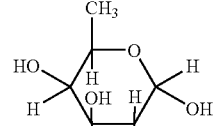

(5) N-fucosegeranamide

The geranylamide derivatives of above formula (I-2) include, for example, the following compounds.

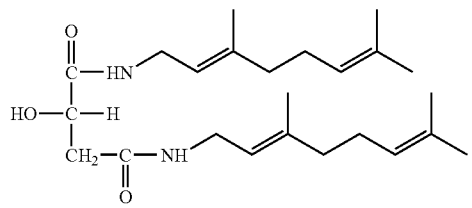

(6) N,N'-digeranylmalic diamide

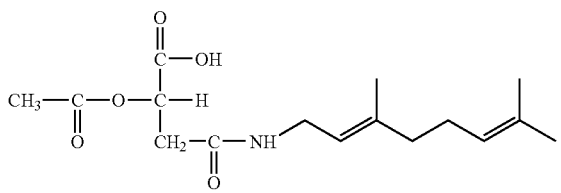

(7) O-acetyl-N-geranylmalic monoamide

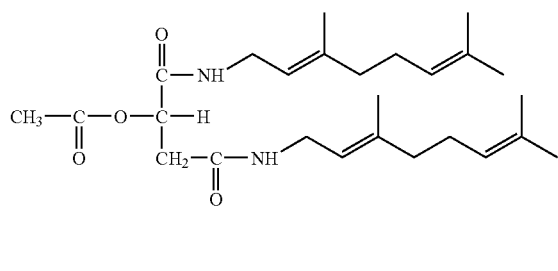

(8) O-acetyl-N,N'-digeranylmalic diamide

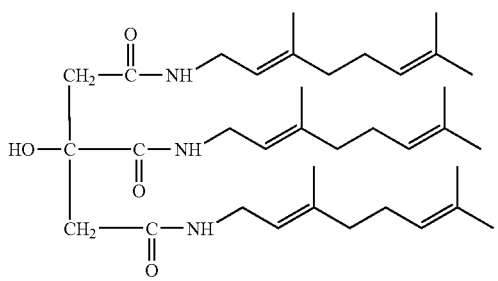

(9) N,N',N''-trigeranylcitric triamide

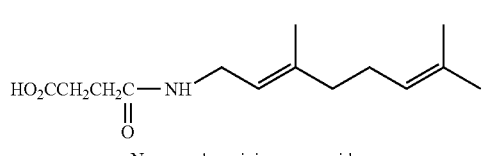

(10) N-geranylsuccinic monoamide

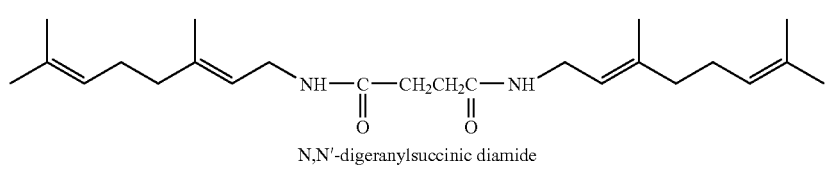

(11) N,N'-digeranylsuccinic diamide

-continued
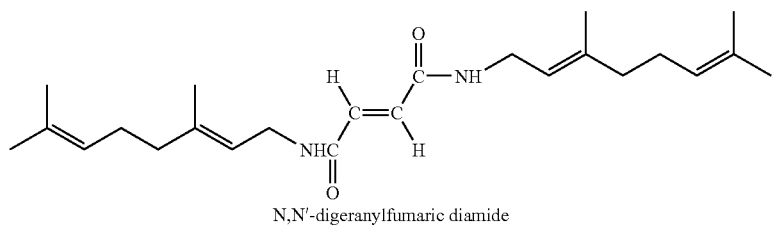
N,N'-digeranylfumaric diamide (12)
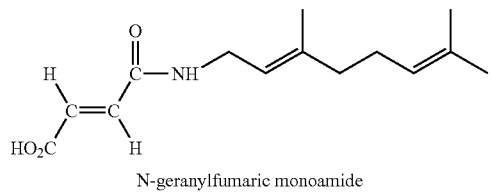
N-geranylfumaric monoamide (13)
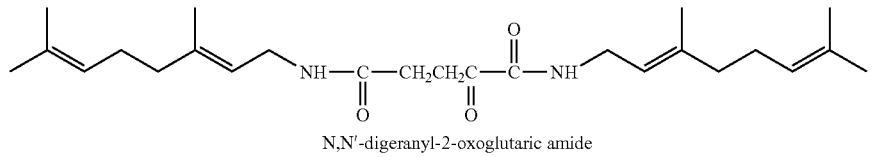
N,N'-digeranyl-2-oxoglutaric amide (14)
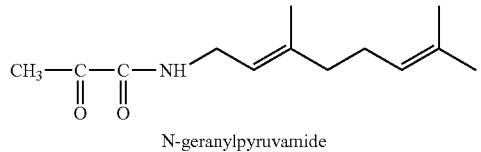
N-geranylpyruvamide (15)
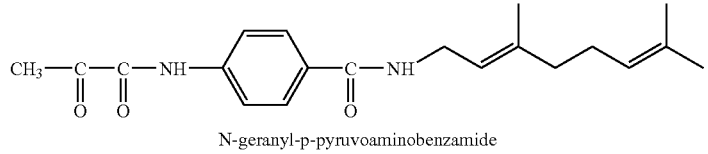
N-geranyl-p-pyruvoaminobenzamide (16)
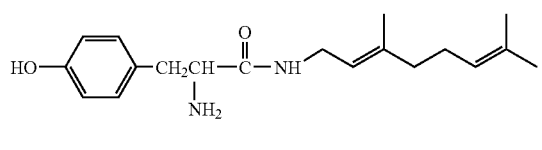
tyrosine geranylamide (17)
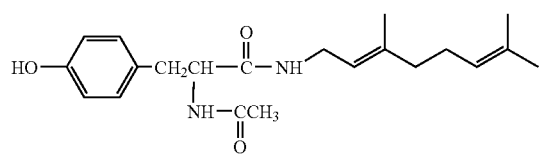
N-acetyltyrosine geranylamide (18)
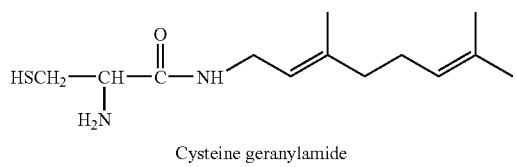
Cysteine geranylamide (19)
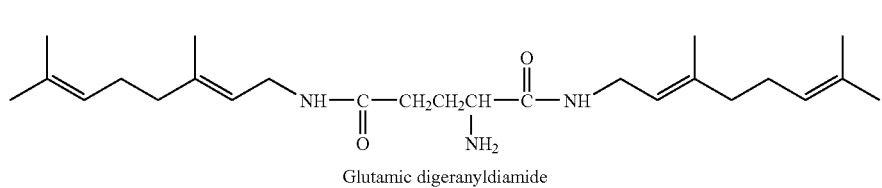
Glutamic digeranyldiamide (20)

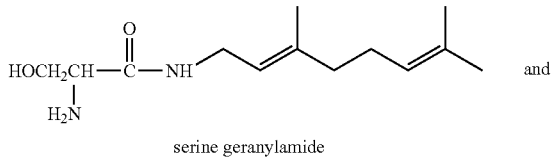

serine geranylamide

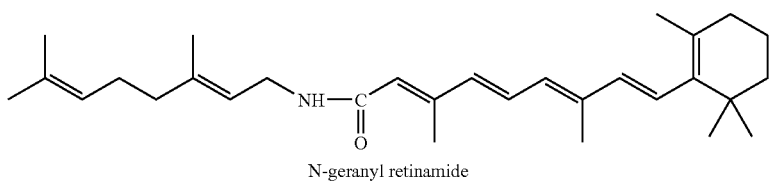

N-geranyl retinamide

Also the geranylamide derivatives of above formula (I-3) include the following two compounds:

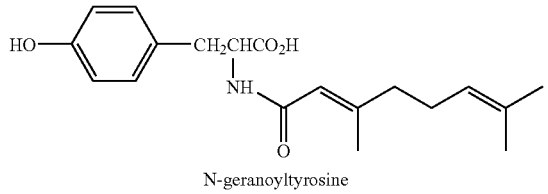

N-geranoyltyrosine

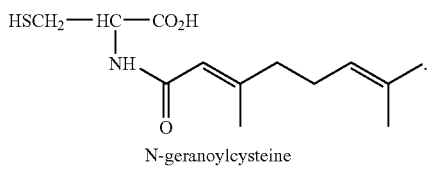

N-geranoylcysteine

The mevalonic acid derivatives of above formula (I-4) include, for example, the following:

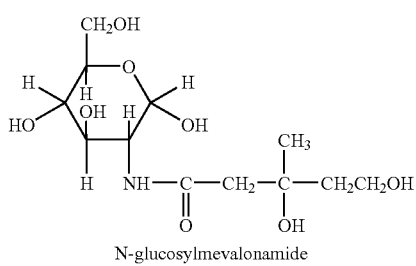

N-glucosylmevalonamide

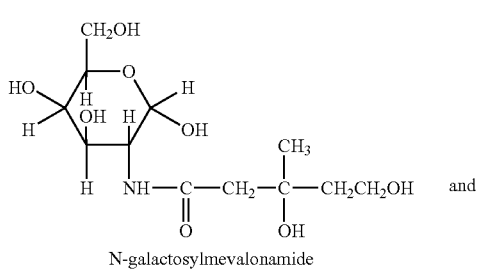

N-galactosylmevalonamide

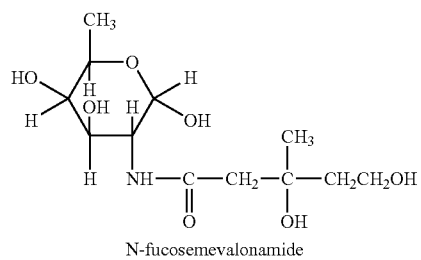

N-fucosemevalonamide

Among the compounds of the formula (I-1), those of the formulae (1) and (2) can be prepared by, for example, subjecting geranylamine to an amidation reaction with reactive derivatives (e.g., mixed acid anhydride, active ester, halide or the like) of glucuronic acid or galacturonic acid whose hydroxyl group(s) are protected with acyl group(s) (e.g., acetyl).

Of the compounds of the formula (I-1), those of the formulae (3) to (5) can be prepared by, for example, subjecting reactive derivatives of geranic acid (e.g., mixed acid anhydride, active ester, halide or the like) to an amidation reaction with galactosamine, glucosamine or fucosamine.

Said amidation reaction can be conducted following the conventional method of amidation reaction in the field of peptide chemistry, normally in an adequate inert organic solvent (e.g., tetrahydrofuran, chloroform, N,N-dimethylformamide, dichloromethane or the like) or in water, under cooling down to about 0° C. or heating up to about 60° C., preferably at about 0° C. to room temperature.

The use ratio of geranylamine to a reactive derivative of gulcuronic acid or galacturonic acid whose hydroxyl group(s) are protected is not strictly limited, but it is normally preferred to use the geranylamine within a range of 1-2 moles, per mole of the reactive derivative.

The use ratio of galactosamine, glucosamine or fucosamine to a reactive derivative of geranic acid is again not strictly limited, but normally it is preferred to use galactosamine, glucosamine or fucosamine within a range of 1-2 moles, per mole of the reactive derivative.

Where hydroxyl-protective groups are present after the amidation reaction, said protective groups are removed by a de-protection reaction such as hydrolysis, to provide geranyl-sugar derivatives of the formula (I-1).

The geranyl-sugar derivatives of the formula (I-1) produced through above reactions can be isolated from the reaction mixtures and purified by conventional means, for example, extraction, crystallization, chromatography or the like.

The geranylamide derivatives of the above formula (I-2) can be produced by, for example, subjecting geranylamine to an amidation reaction with reactive derivatives (e.g., mixed acid anhydride, active ester, halide or the like) of carboxylic acid represented by the formula (II):

(II)

in which $R^2$, m and n have the earlier given significations, in which hydroxyl or amino group(s) are protected with acyl (e.g., lower alkanoyl such as acetyl), benzyloxycarbonyl and the like groups.

Said amidation reaction can be conducted following the conventional method of amidation reaction in the field of peptide chemistry, normally in an adequate inert organic solvent (e.g., tetrahydrofuran, ether, dichloromethane, chloroform, N,N-dimethylformamide or the like) under cooling down to about 0° C. or heating up to about 60° C., preferably at about 0° C. to room temperature.

The use ratio of geranylamine to a reactive derivative of carboxylic acid of the formula (II) is variable depending on the number of geranyl group (m) to be introduced into the carboxylic acid, while it is normally preferred to use it within a range of 1 mole to (m+2) moles per mole of the reactive derivative.

When the hydroxyl- or amino-protective groups are present after the amidation reacetion, they are removed where necessary by a de-protection reaction such as hydrolysis to provide geranyl amide derivatives of the formula (I-2).

Those geranylamide derivatives of the formula (I-3) can be prepared by, for example, subjecting reactive derivatives of geranic acid (e.g., mixed acid anhydride, active ester, halide and the like) to an amidation reaction with tyrosine or cysteine.

This amidation reaction can also be conducted following conventional method of amidation reaction in the field of peptide chemistry, normally in an adequate inert organic solvent (e.g., tetrahydrofuran, ether, dichloromethane, chloroform, N,N-dimethylformamide or the like) or in water, under cooling down to about 0° C. or heating up to about 60° C., preferably at about 0° C. to room temperature.

The use ratio of tyrosine or cysteine to a reactive derivative of geranic acid is not strictly limited, but it is normally preferred to use either of them within a range of 1-2 moles per mole of the reactive derivative.

Such geranylamide derivatives of the formula (I-2) or (I-3) produced in the above reactions can be isolated from the reaction mixtures and purified by conventional means, for example, extraction, crystallization, chromatography or the like.

Those mevalonic acid derivatives of the formula (I-4) can be prepared, for example, by reacting sugaramine represented by the following formula:

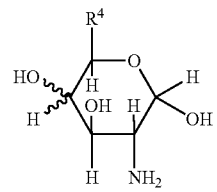

(III)

in which $R^4$ has the earlier given signification, or salt thereof with mevalolactone or mevaloyl halide.

Said reaction of a sugaramine of the formula (III) or a salt thereof with mevalolactone or mevaloyl halide (e.g., mevaloyl chloride) can be conducted in water or an adequate inert organic solvent (e.g., N,N-dimethylformamide, tetrahydrofuran, chloroform or the like) at temperatures between room temperature to reflux temperature of the solvent, preferably from about 40° to about 70° C.

The use ratio of mevalolactone or mevaloyl halide to a sugaramine of the formula (III) is not strictly limited, but it is normally preferred to use 1-2 moles of mevalolactone or mevaloyl halide per mole of the sugaramine of the formula (III).

Where a salt of a sugaramine of the formula (III) or mevaloyl halide is used as the starting material, it is generally desirable to carry out the above reaction with addition of a base, for example, tertiary amine such as N-methylpiperidine; or an inorganic base such as sodium hydroxide, potassium hydroxide, potassium carbonate and the like.

The mevalonic acid derivatives of the formula (I-4) produced through above reactions can be isolated from the reaction mixtures and purified by conventional means, such as extraction, crystallization, chromatography or the like.

Compounds of the formulae (I-1) through (I-4) offered by the present invention possess excellent antitumor activity, as is clear from the following measurement results of antitumor effect.

Measurement of Antitumor Effect

Carcinoma of HuH-7 cells (dendriform cell strain of human hepatoma) hypodermically implanted or subimplanted in the backs of 5-weeks old female nude mice (BALB/c, Ninox) was aseptically taken out and crushed into 5×5 mm sized pieces in a phosphate buffer solution (PBS), a piece of which then being hypodermically implanted in the backs of the nude mice.

Each test substance was dissolved in corn oil, and the solution was intraperitoneally administered to the nude mice consecutively once per day at a rate of 250 μg/mouse for 3 weeks, starting from a week after the implantation. After termination of the administration, the carcinomas were taken out and weighed to calculate the antitumor effect and the mice' weight loss by the following equations. For the test six mice per group were used, and the group administered with the solvent (corn oil) alone was made the control group:

$$\text{Antitumor effect (\%)} = \frac{\text{average tumor weight of a test group}}{\text{average tumor weight of the control group}} \times 100$$

$$\text{Weight loss (\%)} = \frac{\text{average body weight of a test group mice}}{\text{average body weight of the control group mice}} \times 100$$

Evaluations of antitumor effect and weight loss were conducted according to the following standard, where the control group values were held to be 100%.

Antitumor Effect
  −: >100%, +/−: 100~75%, +: 75~50%, ++: 50~25%, +++: 25~0%

Weight Loss
  −: >110%, +/−: 110~100%, +: 100~95%, ++: 95~90%, +++: <90%

Death Rate (Death Rate During the Test Period)
  −: none
  +/−: death occurred with high concentration administration (500 μg/mouse)
  +: 1-3 mice dead
  ++: 3-5 mice dead
  +++: all 6 mice dead Synthetic Evaluation
  −: weak antitumor effect and very strong toxicity against host mice
  +/−: weak antitumor effect recognizable and toxicity against host mice also observable
  +: a fixed level of antitumor effect observable but toxicity against host mice also strong
  ++: strong antitumor effect observed and toxicity against host mice week
  +++: strong antitumor effect observed and no toxicity against host mice The results are shown in the following Tables 1-3.

TABLE 1

| Test Substance | Antitumor Effect | Toxicity Weight loss | Death rate | Synthetic Evaluation |
| --- | --- | --- | --- | --- |
| N-geranyl gulonamide | ++ | +/− | − | ++ |
| N-geranyl galacturonamide | +++ | +/− | +/− |  |
| N-galactosylgeranamide | +++ | + | − | +++ |
| N-fucosegeranamide | ++ | +/− | − | +++ |

TABLE 2

| Test Substance | Antitumor Effect | Toxicity Weight loss | Death rate | Synthetic Evaluation |
| --- | --- | --- | --- | --- |
| N,N'-digeranylmalic diamide | + | + | − | ++ |
| N,N'-digeranylfumaric diamide | ++ | +/− | − | ++ |
| N-geranyl-4-pyruvoaminobenzamide | ++ | − | − | +++ |
| N-geranoyltyrosine | ++ | +/− | − | ++ |

TABLE 2-continued

| Test Substance | Antitumor Effect | Toxicity Weight loss | Death rate | Synthetic Evaluation |
| --- | --- | --- | --- | --- |
| Tyrosine geranylamide | + | +/− | − | + |
| N-acetyltyrosine geranylamide | + | +/− | − | + |

TABLE 3

| Test Substance | Antitumor Effect | Toxicity Weight loss | Death rate | Synthetic Evaluation |
| --- | --- | --- | --- | --- |
| N-glucosylmevalonamide | ++ | +/− | − | +++ |

As is clear from the shown results, the compounds of the invention of the formulae (I-1) to (I-4) possess excellent antitumor effect against HuH-7 cells and furthermore almost no toxicity, and are expected to be useful as antitumor agents for treatment and therapy of various solid cancer represented by liver cancer.

Where a compound of the present invention is used as a medicine such as an antitumor agent, it can be administered orally or parenterally (e.g., intravenous injection, intramuscular injection, hypodermic injection, or the like). The effective dose is variable over a broad range depending on individual patients' symptoms, seriousness of the illness, body weight, age, and the doctor's diagnosis, etc. Normally, however, taking a case of administration by injection, the dose can be about 1-about 50 mg/kg/day, which may be administered at a single time or at plural times dividedly in a day.

Where a compound of the present invention is used as a medicine, an effective dose of the compound can be formulated with pharmaceutically acceptable carrier or diluent (e.g., excipient, solvent or other adjuvants) into a preparation form suitable for unit dose administration, for example, tablet, powder, granule, capsule, enteric coated pill, troche, syrup, elixir, liquid, suspension, emulsion and the like.

As carriers or diluents useful for the formulation, for example, excipients such as starch, lactose, sucrose, mannitol, carboxymethyl cellulose and the like; lubricants such as magnesium stearate, sodium laurylsulfate, talc and the like; binders such as dextrin, microcrystalline cellulose, polyvinylpyrrolidone, gum Arabic, corn starch, gelatin and the like; disintegrators such as potato starch, carboxymethyl cellulose and the like; and diluent solvents such as water for injection, physiological saline, aqueous dextrose solution, vegetable oil for injection, propylene glycol, polyethylene glycol and the like can be named. Furthermore, taste- or odor-correcting agent, colorant, isotonicity, stabilizer, antiseptic, soothing agent and the like may be incorporated where necessary.

In the pharmaceutical preparations according to the invention, moreover, other pharmacologically active substance(s) may be incorporated where necessary.

Hereinafter the invention is explained still more specifically, referring to working Examples.

EXAMPLES

Synthesis Example 1

Synthesis of N-geranylgalacturonamide

To a tetrahydrofuran (THF) (20 ml) solution containing O-tetraacetylgalacturonic acid (3.62 g, 10 mmols), triethylamine (1.01 g, 10 mmols) was added, and the solution was cooled to 0° C. Into this solution isobutyl chloroformate (1.37 g, 10 mmols) solution in THF (5 ml) was added dropwise at 0° C., followed by 30 minutes' stirring. Into the resulting solution a geranylamine (1.53 g, 10 mmols) solution in THF (5 ml) was added dropwise, followed by an hour's stirring at 0° C. and further 4 hours' stirring at room temperature. After termination of the reaction, 150 ml of chloroform was added, and the chloroform layer was washed three times each with 50 ml of water. The chloroform layer was dried over magnesium sulfate, the chloroform was concentrated, and the residue was purified on silica gel column chromatography. Consequently, 3.58 g (73.5%) of N-geranyl-O-tetraacetylgalacturonamide was obtained as a viscous oily substance, from its hexane-acetone (3:1) distillate.

$^1$H NMR (CDCl$_3$) δ=1.58 (3H, s), 1.65 (3H, s), 1.68 (3H, s), 2.01 (3H, s), 2.02 (3H, s), 2.05 (3H, s), 2.15 (3H, s), 2.02-2.11 (4H, m), 3.70-3.83 (1H, m), 3.83-3.96 (1H, m), 5.00-5.17 (2H, m), 5.29 (1H, d, J=10.8 Hz), 5.39 (1H, d, J=10.8 Hz), 6.29-6.46 (2H, m).

3.58 Grams (7 mmols) of above product was dissolved in 30 ml of ethanol, 35 ml of 1N aqueous sodium hydroxide solution was added, and stirred for 2 hours at room temperature. Then 35 ml of 1N hydrochloric acid was added to the reaction mixture and condensed under reduced pressure. To the residue 150 ml of ethanol was added and precipitated sodium chloride was filtered off. The filtrate was again condensed, and the residue was separated on silica gel column chromatography. From the hexane-ethanol (3:1) distillate, 1.95 g of N-geranylgalacturonamide was obtained as a viscous compound. Ether was added to this product to conduct crystallization, and by suction filtration 1.03 g of crystallized title compound was obtained. The yield was 45%.

$^1$H NMR (DMSO-d6) δ=1.50 (3H, s), 1.55 (3H, s), 1.56 (3H, s), 1.86-2.04 (4H, m), 3.48-3.76 (2H, m), 3.80-3.94 (2H, m), 4.07-4.84 (3H, m), 4.99 (1H, d, J=9.6 Hz), 5.06 (1H, d, J=9.6 Hz).

Synthesis Example 2

Synthesis of N-geranylgulcronamide

Synthesis Example 1 was repeated except that O-tetraacetylglucuronic acid was used in place of O-tetraacetylgalacturonic acid, to provide the title compound.

$^1$H NMR (DMSO-d6) δ=1.60 (3H, s), 1.68 (3H, s), 1.73 (3H, s), 2.07-2.09 (4H, m), 3.58-3.62 (2H, m), 3.81-3.95 (2H, m), 4.07-4.86 (3H, m), 5.05-5.09 (1H, m), 5.36-5.40 (1H, m).

Synthesis Example 3

Synthesis of N-galactosylgeranamide

To a THF (20 ml) solution containing geranic acid (0.84 g, 5 mmols), triethylamine (0.51 g, 5 mmols) was added and cooled to 0° C., into which a THF (5 ml) solution containing isobutyl chloroformate (0.68 g, 5 mmols) was added dropwise, followed by 30 minutes' stirring at 0° C. Then galactosamine hydrochloride (1.08 g, 5 mmols) was dissolved in 10 ml of water, to which 5 ml of 1N sodium hydroxide was further added, and the solution was added to the reaction mixture all at a time. After the following stirring for an hour at 0° C. and for further 4 hours at room temperature, the reaction mixture was condensed under reduced pressure. To the residue 150 ml of acetone was added and precipitated sodium chloride was filtered off. The filtrate was condensed once again and the residue was separated on silica gel column chromatography. Consequently the product was obtained from the hexane-ethanol (2:1) distillate as a viscous oily substance, to which a minor amount of ether was added to crystallize the product. Through subsequent suction filtration, 0.754 g of the title compound was obtained. The yield was 46%, and the melting point was 85-87° C.

$^1$H NMR (DMSO-d6)δ=1.53 (3H, s), 1.57 (3H, s), 1.59 (3H, s), 1.95-2.01 (4H, m), 3.63-3.79 (7H, m), 4.25-4.60 (3H, m), 4.85-4.92 (1H, m), 5.00-5.08 (1H, m), 6.25-6.31 (1H, m).

Synthesis Example 4

Synthesis of N-glucosylgeranamide

Synthesis Example 3 was repeated except that glucosamine hydrochloride was used in place of galactosamine hydrochloride, to provide the title compound.

$^1$H NMR (DMSO-d6) δ=1.54 (3H, s), 1.60 (3H, s), 2.03 (3H, s), 1.96-2.20 (4H, m), 3.38-3.61 (4H, m), 4.38-4.66 (3H, m), 5.75 (1H, s), 6.34-6.39 (1H, m).

Synthesis Example 5

Synthesis of N-fucosegeranamide

Synthesis Example 3 was repeated except that fucosamine hydrochloride was used in place of galactosamine hydrochloride, to provide the title compound.

$^1$H NMR (DMSO-d6) δ=1.31 (3H, d, J=5.4 Hz), 1.53 (3H, s), 1.60 (3H, s), 1.72 (3H, s), 1.97-2.05 (4H, m), 3.88-3.95 (2H, m), 4.21-4.24 (1H, m), 4.44-4.46 (1H, m), 4.82-4.87 (1H, m), 5.00-5.13 (1H, m).

Synthesis Example 6

Synthesis of N,N'-digeranylfumaric diamide

To a tetrahydrofuran (THF) (20 ml) solution containing fumaric acid (0.58 g, 5 mmols), triethylamine (1.01 g, 10 mmols) was added and the solution was cooled to 0° C., into which a THF (5 ml) solution containing isobutyl chloroformate (1.53 g, 10 mmols) was added dropwise. As the addition was continued, white precipitate started to form. After 30 minutes' stirring at 0° C., a THF (5 ml) solution containing geranylamine (1.53 g, 10 mmols) was added dropwise into the system, followed by an hour's stirring at 0° C. and further 4 hours' stirring at room temperature. After termination of the reaction, 50 ml of water was added to the reaction mixture which was then extracted with chloroform. The chloroform layer was washed with water and dried over magnesium sulfate. Filtering the magnesium sulfate off, the chloroform layer was condensed to provide a white crystal. Recrystallizing the same from ethanol, 1.07 g of the title compound was obtained. The yield was 55%.

$^1$H NMR (CDCl$_3$) δ=1.60 (6H, s), 1.62 (6H, s), 1.68 (6H, s), 2.01-2.10 (8H, m), 3.95 (4H, t, J=9.6 Hz), 5.04-5.09 (2H, m), 5.20-5.25 (2H, m), 5.94 (2H, brs), 6.90 (2H, s), 7.26 (2H, s).

Synthesis Example 7

Synthesis Example 6 was repeated except that the fumaric acid was replaced with corresponding carboxylic acid of the earlier given formula (II) in each run, to provide the following compounds:

N-geranylpyruvamide
$^1$H NMR (CDCl$_3$) δ=1.55 (3H, s), 1.64 (3H, s), 1.82 (3H, s), 2.00 (3H, s), 1.92-2.12 (4H, m), 3.84 (2H, d, J=7.2 Hz), 4.96-5.12 (1H, m), 5.22-5.35 (1H, m).

N,N'-digeranylmalic diamide
$^1$H NMR (CDCl$_3$) δ=1.58 (6H, s), 1.64 (6H, s), 1.67 (6H, s), 1.94-2.14 (8H, m), 2.54 (1H, dd, J=4.8, 14.8 Hz), 2.79 (1H, dd, J=3.2, 14.4 Hz), 3.75-3.93 (4H, m), 4.32-4.40 (1H, m), 5.00-5.10 (2H, m), 5.10-5.22 (2H, m).

O-acetyl-N-geranylmalic monoamide
$^1$H NMR (CDCl$_3$) δ=1.60 (3H, s), 1.68 (3H, s), 1.69 (3H, s), 1.96-2.11 (4H, m), 2.19 (3H, s), 2.65 (1H, dd, J=9.6, 22.8 Hz), 3.00 (1H, dd, J=2.4, 22.8 Hz) 3.79-3.89 (2H, m), 4.51-4.56 (1H, m), 5.08 (1H, t, J=7.2 Hz), 5.18 (1H, t, J=6.0 Hz).

O-acetyl-N,N'-digeranylmalic diamide, which was synthesized by a similar method, using N-geranylmalic acid monoamide as the starting material.
$^1$H NMR (CDCl$_3$) δ=1.59 (6H, s), 1.67 (6H, s), 1.68 (6H, s), 1.94-2.01 (8H, m), 2.16 (3H, s), 2.55 (1H, dd, J=13.2, 22.8 Hz), 2.97 (1H, dd, J=2.4, 22.8 Hz), 3.79-3.89 (4H, m), 4.34-4.40 (1H, m), 5.02-5.10 (2H, m), 5.10-5.20 (2H, m).

N,N',N''-trigeranylcitric triamide
$^1$H NMR (CDCl$_3$) δ=1.60 (9H, s), 1.66 (9H, s), 1.68 (9H, s), 1.98-2.08 (12H, m), 3.76 (6H, t, J=6.3 Hz), 4.26 (4H, s), 5.07 (6H, t, J=6.0 Hz), 5.20 (6H, t, J=7.2 Hz).

N-geranylsuccinic Monoamide
$^1$H NMR (CDCl$_3$) δ=1.60 (3H, s), 1.70 (3H, s), 1.72 (3H, s), 1.92-2.15 (4H, m), 2.52 (2H, t, J=9.6 Hz), 2.70 (2H, t, J=9.6 Hz), 3.80-3.90 (2H, m), 5.08 (1H, t, J=9.6 Hz), 5.18 (1H, t, J=6.0 Hz), 5.61 (1H, brs).

N,N'-digeranylsuccinic diamide, which was synthesized by a similar method, using N-geranylsuccenic monoamide as the starting material.
$^1$H NMR (CDCl$_3$) δ=1.60 (6H, s), 1.66 (6H, s), 1.69 (6H, s), 1.97-2.11 (4H, m), 2.53 (4H, s), 3.84 (4H, t, J=5.5 Hz), 5.07 (2H, t, J=4.9 Hz), 5.17 (2H, t, J=5.5 Hz), 5.90 (2H, brs).

N-geranylfumaric monoamide
$^1$H NMR (CDCl$_3$) δ=1.59 (3H, s), 1.67 (3H, s), 1.70 (3H, s), 1.94-2.16 (4H, m), 3.88-4.04 (2H, m), 5.06 (1H, t, J=7.2 Hz), 5.21 (1H, t, J=4.8 Hz), 6.30 (1H, d, J=12.0 Hz), 6.46 (1H, d, J=12.0 Hz).

N,N'-digeranyl-2-oxoglutaric diamide
$^1$H NMR (CDCl$_3$) δ=1.60 (6H, s), 1.68 (12H, s), 1.94-2.13 (8H, m), 2.69 (2H, t, J=6.3 Hz), 3.26 (2H, t, J=6.3 Hz), 3.81-4.04 (4H, m), 5.02-5.10 (2H, m), 5.15-5.22 (2H, m).

N-geranyl-p-pyruvoaminobenzamide
$^1$H NMR (CDCl$_3$) δ=1.60 (3H, s), 1.68 (3H, s), 1.70 (3H, s), 2.03-2.11 (4H, m), 2.17 (3H, s), 3.95-4.04 (2H, m), 4.83 (1H, brs), 5.09 (1H, t, J=6.6 Hz), 5.28 (1H, t, J=6.9 Hz), 5.94 (1H, brs), 6.64 (2H, d, J=8.7 Hz), 7.60 (2H, d, J=8.7 Hz).

N-geranylretinamide
$^1$H NMR (CDCl$_3$) δ=1.03 (6H, s), 1.12-1.63 (6H, m), 1.60 (3H, s), 1.66 (3H, s), 1.68 (3H, s), 1.72 (3H, s), 1.87-1.93 (4H, m), 2.01 (3H, s), 2.37 (3H, s), 3.82-3.92 (2H, m), 5.03-5.24 (2H, m), 5.80 (1H, s), 6.12-6.40 (3H, m), 7.02 (1H, d, J=12.0 Hz), 7.07 (1H, d, J=12.0 Hz).

Synthesis Example 8

Synthesis of N-geranoylcysteine

To a THF (20 ml) solution containing geranic acid (1.68 g, 10 mmols), triethylamine (1.01 g, 10 mmols) was added and cooled to 0° C., into which a THF (5 ml) solution of isobutyl chloroformate (1.37 g, 10 mmols) was added dropwise, followed by 30 minutes' stirring at 0° C. To the reaction mixture a solution of cysteine (1.35 g, 10 mmols) as dissolved in 1N sodium hydroxide (10 ml) was added, followed by an hour's stirring at 0° C. and further 4 hours' stirring at room temperature. After termination of the reaction, 10 ml of 1N hydrochloric acid was added to the reaction mixture and stirred for 10 minutes at room temperature. Then the reaction mixture was condensed with a rotary evaporator. To the residue ethanol was added, and whereupon precipitated sodium chloride was removed by filtration. The ethanol solution was once again condensed under reduced pressure with the evaporator, and the residue was separated on silica gel column chromatography. Thus 0.556 g of the title compound was obtained from the hexane-acetone (2:1) distillate. The yield was 19.5%:
$^1$H NMR (CDCl$_3$)δ=1.59 (6H, s), 1.68 (3H, s), 2.00-2.24 (4H, m), 2.60-2.77 (1H, m), 3.00-3.30 (2H, m), 4.48-4.58 (1H, m), 5.00-5.13 (1H, m), 8.96 (1H, s).

Synthesis Example 9

N-geranoyltyrosine

Synthesis Example 8 was repeated except that the cysteine was replaced with tyrosine, to provide the title compound:
$^1$H NMR (CDCl$_3$)δ=1.55 (6H, s), 1.64 (3H, s), 1.96-2.00 (4H, m), 2.90-3.17 (2H, m), 4.81-5.06 (3H, m), 6.40-7.21 (4H, m), 7.25 (1H, s).

Synthesis Example 10

Synthesis of Glutamic Digeranyldiamide

To a THF (20 ml) solution of N-benzyloxycarbonylglutamic acid (2.634 g, 9.4 mmols), triethylamine (1.899 g, 18.8 mmols) was added and cooled to 0° C. Into this mixture a THF (10 ml) solution of isobutyl chloroformate (2.566 g, 18.8 mmols) was added dropwise, followed by 30 minutes' stirring at 0° C. Then a THF (10 ml) solution of geranylamine (2.880 g, 18.8 mmols) was added dropwise, followed by an hour's stirring at 0° C. and further 4 hours' stirring at room temperature. After termination of the reaction, 150 ml of chloroform was added to the system, and the chloroform solution was washed with water and dried over magnesium sulfate. The organic solvent was removed with an evaporator and the residue was separated on silica gel column chromatography. Thus 3.034 g of N-benzyloxycarbonylglutamic digeranyldiamide was obtained from the hexane-acetone (2:1) distillate. The yield was 58.6%.

Then the N-benzyloxycarbonylglutamic digeranyldiamide (3.034 g, 5.5 mmols) was dissolved in methanol (20 ml), and to the same solution 20 ml of 1N sodium hydroxide was added, followed by 5 hours' stirring at room temperature. The reaction mixture was condensed with an evaporator, and the residue was separated on silica gel column chromatography to provide the object compound from the hexane-ethanol (3:1) distillate. Because the as-obtained product was viscous and amorphous, ether was added to the product for crystallization. Upon suction-filtering the system, 852 mg of the object compound was obtained. The yield was 37.2%:

$^1$H NMR (CDCl$_3$)δ=1.58 (12H, s), 1.61 (6H, s), 1.75-2.12 (8H, m), 2.32-2.53 (2H, m), 3.54-3.88 (7H, m), 4.88-5.21 (4H, m).

Synthesis Example 11

Repeating Synthesis Example 10 except that N-benzyloxycarbonylglutamic acid was replaced with tyrosine, N-acetyltyrosine, cysteine or serine, the following compounds, respectively, were obtained. Where N-acetyltyrosine was used, the later deprotection operation was not conducted.

Tyrosine Geranylamide $^1$H NMR (CDCl$_3$)δ=1.59 (3H, s), 1.67 (6H, s), 1.82-2.18 (4H, m), 2.99-3.09 (2H, m), 3.74-3.78 (2H, m), 4.99-5.26 (3H, m), 7.17-7.43 (5H, m).

N-acetyltyrosine Geranylamide $^1$H NMR (CDCl$_3$)δ=1.60 (3H, s), 1.68 (3H, s), 1.98 (3H, s), 2.00-2.11 (4H, m), 2.18 (3H, s), 2.90-3.00 (2H, m), 3.69-3.79 (2H, m), 4.59 (1H, dd, J=15.6, 9.6 Hz), 5.00-5.10 (2H, m), 6.70 (2H, d, J=7.8 Hz), 7.01 (2H, d, J=7.8 Hz), 7.27 (1H, s).

Cysteine Geranylamide $^1$H NMR (CDCl$_3$)δ=1.58 (3H, s), 1.66 (3H, s), 1.67 (3H, s), 1.93-2.10 (4H, m), 2.83-3.16 (2H, m), 3.83-4.08 (3H, m), 5.03-5.19 (2H, m), 7.33 (1H, s).

Serine Geranylamide $^1$H NMR (CDCl$_3$)δ1.59 (3H, s), 1.68 (6H, s), 1.95-2.14 (4H, m), 3.80-3.95 (2H, m), 4.34-4.47 (2H, m), 4.67 (1H, t, J=10.8 Hz), 5.06 (1H, t. J=6.0 Hz), 5.17 (1H, t, J=6.0 Hz), 6.77 (2H, brs).

Synthesis Example 12

Synthesis of N-glucosylinevalonamide

Glucosamine hydrochloride (2.16 g, 10 mmols) was dissolved in 20 ml of water, and to the aqueous solution 10 ml of 1N sodium hydroxide and mevalolactone (1.30 g, 10 mmols) were added, followed by 5 hours' heating under stirring at 55° C. After termination of the reaction, the reaction mixture was condensed under reduced pressure. To the residue 100 ml of methanol was added and whereupon separated precipitate was filtered off. The filtrate was condensed again with an evaporator and the residue was separated on silica gel column chromatography, to provide 1.45 g of the object product from the ethanol distillate. The yield was 47%. Because the as-obtained product was a viscous oily substance, a minor amount of dichloromethane was added thereto to effect crystallization. Upon suction filtering, 1.10 g of the title compound was obtained, which was strongly hygroscopic and its melting point could not be measured:

$^1$H NMR (DMSO-d$_6$) δ=1.00 (3H, s), 1.44-1.59 (2H, m), 2.47 (2H, s), 2.96-3.74 (10H, m), 4.04-5.08 (3H, m).

Synthesis Example 13

Synthesis of N-galactosylmevalonamide

Synthesis Example 12 was repeated except that the glucosamine hydrochloride was replaced with galactosamine hydrochloride, to provide the title compound:

$^1$H NMR (DMSO-d6) δ=1.08 (3H, s), 1.51-1.61 (2H, m), 2.44 (2H, s), 2.74-5.16 (13H, m).

Synthesis Example 14

Synthesis of N-fucosemevalonamide

Synthesis Example 12 was repeated except that the glucosamine hydrochloride was replaced with fucosamine hydrochloride, to provide the title compound:

$^1$H NMR (DMSO-d6) δ=1.06 (3H, s), 1.20 (3H, d, J=24.0 Hz), 1.54-1.62 (2H, m), 2.44 (2H, s), 2.74-5.15 (12H, m).

Formulation Example 1

Two (2) g of N-galactosylgeranamide was dissolved in 1 liter of water for injection at ambient temperature, isotonized with sodium chloride and sealed into ampoules. One (1) ml of this injection contains 2 mg of the active ingredient.

Formulation Example 2

Two (2) g of N,N'-digeranylmalic diamide was dissolved in 1 liter of water for injection at ambient temperature, isotonized with sodium chloride and sealed into ampoules. One (1) ml of this injection contains 2 mg of the active ingredient.

Formulation Example 3

Two (2) g of N-glucosylmevalonamide was dissolved in 1 liter of water for injection at ambient temperature, isotonized with sodium chloride and sealed into ampoules. One (1) ml of this injection contains 2 mg of the active ingredient.

The invention claimed is:
1. A geranyl compound represented by the following formula (I-2):

(I-2)

in which R$^2$ stands for a residual group remaining after removing all carboxyl groups present in a carboxylic acid selected from the group consisting of malic acid, citric acid, succinic acid, fumaric acid, 2-oxoglutaric acid, pyruvic acid, p-pyruvoaminobenzoic acid, retinoic acid, tyrosine, cysteine, glutamic acid and serine, and where hydroxyl or amino group(s) are present in the residual group, they may optionally be protected by acyl or benzyloxycarbonyl group(s), m is 1, 2 or 3, n is 0, 1 or 2, and m +n represents the number of carboxyl groups which are removed from said carboxylic acid.

2. An antitumor agent containing, as an active ingredient, the geranyl compound of the formula (I-2) as claimed in claim 1.

3. A pharmaceutical composition comprising an activity-effective amount of the geranyl compound of the formula (I-2) as claimed in claim 1, and a pharmaceutically acceptable carrier or diluent.

4. A method of treating solid cancers of the liver, comprising administering an antitumorically effective amount of the geranyl compound of the formula (I-2) as claimed in claim 1 to a patient in need thereof.

5. A method of making the pharmaceutical composition according to claim 3, which comprises mixing the geranyl compound of the formula (I-2) with the pharmaceutically acceptable carrier or diluent.

* * * * *